(12) United States Patent
Pang et al.

(10) Patent No.: US 7,245,698 B2
(45) Date of Patent: Jul. 17, 2007

(54) 4-DIMENSIONAL DIGITAL TOMOSYNTHESIS AND ITS APPLICATIONS IN RADIATION THERAPY

(75) Inventors: Geordi G. Pang, Markham (CA); Ali Bani-Hashemi, Walnut Creek, CA (US); John Alan Rowlands, Toronto (CA)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 11/181,339

(22) Filed: Jul. 13, 2005

(65) Prior Publication Data

US 2007/0025509 A1 Feb. 1, 2007

(51) Int. Cl.
*A61N 5/10* (2006.01)
(52) U.S. Cl. .......................................... 378/65; 378/22
(58) Field of Classification Search ................. 378/65, 378/21–26
See application file for complete search history.

(56) References Cited

U.S. PATENT DOCUMENTS

| 5,872,828 | A | 2/1999 | Niklason et al. ............... 378/23 |
| 6,196,715 | B1* | 3/2001 | Nambu et al. ............... 378/197 |
| 6,574,629 | B1* | 6/2003 | Kaufman et al. ............. 707/10 |
| 6,618,467 | B1* | 9/2003 | Ruchala et al. ................ 378/65 |
| 6,842,502 | B2* | 1/2005 | Jaffray et al. .................. 378/65 |
| 6,862,337 | B2 | 3/2005 | Claus et al. ................... 378/26 |
| 7,127,028 | B2* | 10/2006 | Sendai ......................... 378/21 |
| 2005/0251010 | A1* | 11/2005 | Mistretta et al. ............. 600/407 |
| 2006/0067473 | A1* | 3/2006 | Eberhard et al. ........... 378/98.9 |
| 2006/0098856 | A1* | 5/2006 | Botterweck et al. ........ 382/131 |
| 2006/0133564 | A1* | 6/2006 | Langan et al. .................. 378/8 |

OTHER PUBLICATIONS

Vedam et al., Acquiring a four-dimensional computed tomography dataset using an external respiratory signal, Dec. 16, 2002, Phys. Med. Biol., vol. 48, pp. 45-62.*
Underberg et al., Four-dimensional CT scans for treatment planning in stereotactic radiotherapy for stage I lung cancer, Int. J. Radiation Oncology Bio. Phys., Oct. 29, 2004, vol. 60, No. 4, pp. 1283-1290.*

(Continued)

*Primary Examiner*—Edward J. Glick
*Assistant Examiner*—John M. Corbett

(57) ABSTRACT

A 4-dimensional digital tomosynthesis system includes an x-ray source, an x-ray detector and a processor. The x-ray source is suitable for emitting x-ray beams to an object with a periodic motion. The periodic motion is divided into (n+1) time intervals, n being a positive integer. Each of the (n+1) time intervals is associated with a time instance $t_i$, i=0, 1, 2, . . . , n. The x-ray detector is coupled to the x-ray source for acquiring projection radiographs of the object at each time instance $t_i$ for each scan angle based on the x-ray beams. The processor is communicatively coupled to the x-ray source and the x-ray detector for controlling the x-ray source and processing data received from the x-ray detector such that all projection radiographs acquired from all scan angles for each time instance $t_i$ are reconstructed and (n+1) sets of cross sections of the object are obtained. The cross section is either a coronal cross section or a sagittal cross section. Each of the (n+1) sets of cross sections is for a different time instance $t_i$.

19 Claims, 12 Drawing Sheets

OTHER PUBLICATIONS

Baydush et al., Initial application of digital tomosynthesis with on-board imaging in radiation oncology, Conference date Feb. 13, 2005, Proc. SPIE vol. 5745, pp. 1300-1305, Medical Imaging 2005:Physics of medical Imaging, Michael J. Flynn, Editor, Apr. 2005.*

Rietzel et al., Four-Dimensional Image-based treatment planning: target volume segmentation and dose calculation in the presence of respiratory motion, Apr. 1, 2005, International Journal of Radiation Oncology, vol. 61, No. 5, pp. 1535-1550.*

R. Robinson, Nov. 7, 2002, Invitiation for sealed bid #638324A, Virginia Polytechnic Institute and State University.*

Messaris et al., Three-dimensional localisation based on projectional and tomographic image correlation: an application for digital tomosynthesis, 1999, Medical Engineering & Physics, 21, p. 101-109.*

*Digital X-Ray Tomosynthesis: Current State of the Art and Clinical Potential* by James T. Dobbins III and Devon J. Godfrey; Institute of Physics Publishing, Physics in Medicine and Biology; Phys. Med. Biol. 48 (2003) pp. R65-R106; © 2003 IOP Publishing Ltd.

Three-dimensional dose reconstruction of breast cancer treatment using portal imaging; R. J. W. Louwe, E. M. F. Damen, M. van Herk, A. W. H. Minken, O. Törzsök, and B. J. Minnheer; The Netherlands Cancer Institute/ANtoni van Leeuwénhoek Hospital, Department of Radiotherapy, Amsterdam, The Netherlands; pp. 2376-2389; Med. Phys. 30 (9), Sep. 2003; © 2003 Am. Assoc. Phys. Med.

Mega Voltage Cone Beam Reconstruction; http://www.ucsf.edu/jpouliot/Course/Lesson22.html.

* cited by examiner

4-DIMENSIONAL DIGITAL TOMOSYNTHESIS AND ITS APPLICATIONS IN RADIATION THERAPY

BACKGROUND OF THE INVENTION

The present invention relates generally to the field of x-ray imaging, and more particularly to 4-dimensional (4D) digital tomosynthesis and its applications in radiation therapy.

Digital tomosynthesis (DTS) reconstructs structures existing within an imaged object from a set of projection radiographs. In medical applications, these structures include, for example, anatomical structures such as organs, blood vessels, and bones. In computed tomography (CT), both an x-ray source and an x-ray detector move on a circular trajectory around a common axis, and a very high number of projection radiographs (or images) is acquired. In contrast, in tomosynthesis, relatively few radiographs are acquired for varying x-ray source positions. Tomosynthesis, then, is a system and method that acquires a plurality of projection radiographs, which is not enough for exact computed tomography. In tomosynthesis, typically the x-ray source assumes positions that are essentially on one side of the object, while the detector (or film) assumes positions on the opposite side of the object.

DTS is a method of reconstructing cross sections of a 3D body from its 2D radiographic projections, which is a much faster method than the CT approach for obtaining cross sections. In CT, projections must be acquired from at least 180 degrees plus the fan angle around the object to produce an exact reconstruction of the object. DTS, however, exploits projections from limited angles to reconstruct cross sections of the object. Although the reconstruction is less precise, and the plane of reconstruction is limited to one orientation only, it has the benefit of using a smaller number of projections, i.e. scan angle. This translates into faster data acquisition and provides the advantage of being able to reconstruct objects where space and size limitations prevent one from acquiring projections from all angles. In some clinical situations, exact reconstruction is not necessary, making a fast DTS ideal.

A DTS system includes an x-ray source and a digital detector which are connected to each other by an appropriate mechanical structure. In conventional 3-D DTS, a number of 2-dimensional projection radiographs of a stationary imaged object is acquired at different positions of the x-ray source relative to the imaged object, and from the data sets corresponding to the 2-dimensional projection radiographs, cross sections of the imaged object are reconstructed.

Cone Beam Computed Tomography (CBCT) is expected to play a significant role in radiation therapy. However, due to safety concerns the maximum speed of gantry rotation (e.g., for a Linac machine) is currently limited to ~1.0 rpm (rotation per minute). As a result, data acquisition for CBCT is typically long (on the order of one minute). To ensure image quality, the subject must be motionless during the acquisition. However, there are certain physiological motions such as breathing that cannot be stopped for the duration of acquisition. Therefore, motion artifacts will always plague slow CBCT data acquisition.

It is desired to reconstruct 3D cross sections of time-varying objects at different time instances of the physiological cycle. For example, it would be beneficial to show cross sections of a patient's lungs during the entire breathing cycle. That would allow clinicians to pinpoint the location of a time varying lung tumor at every phase of the breathing cycle. Thus, they would be able to locate and delineate the tumor at exhalation.

Consequently, it would be desirable to provide a new digital tomosynthesis system and method in 4D radiation therapy where the time component is integrated into the three-dimensional (3D) radiation therapy process to deliver dose in view of target motion.

SUMMARY OF THE INVENTION

Accordingly, the present invention is directed to 4-dimensional digital tomosynthesis and its applications in radiation therapy. In an exemplary embodiment, a 4-dimensional digital tomosynthesis system includes an x-ray source, an x-ray detector and a processor. The x-ray source is suitable for emitting x-ray beams to an object with a periodic motion such as breathing motion, or the like. The periodic motion is divided into (n+1) time intervals, n being a positive integer. Each of the (n+1) time intervals is associated with a time instance $t_i$, i=0, 1, 2, ..., n. The x-ray detector is coupled to the x-ray source for acquiring projection radiographs of the object at each time instance $t_i$ for each scan angle based on the x-ray beams. The processor is communicatively coupled to the x-ray source and the x-ray detector for controlling the x-ray source and processing data received from the x-ray detector such that all projection radiographs acquired from all scan angles for each time instance $t_i$ are reconstructed and (n+1) sets of cross sections of the object are obtained. The cross section is either a coronal cross section or a sagittal cross section. Each of the (n+1) sets of cross sections is for a different time instance $t_i$.

In an additional exemplary embodiment, a radiation therapy apparatus capable of implementing 4-dimensional digital tomosynthesis for simultaneous tomographical imaging and treatment includes an imaging system and a treatment system. The imaging system includes a first x-ray source and a first x-ray detector for obtaining tomographical images of a treatment target for geometrical verification. The first x-ray source and the first x-ray detector are isocentric with an isocenter. The treatment target is an object with a motion. The first x-ray source is suitable for emitting x-ray beams to the object. The first x-ray detector is suitable for acquiring projection radiographs of the object for each scan angle based on the x-ray beams. The treatment system includes a second x-ray source and a second x-ray detector for dose delivery and dose reconstruction. The second x-ray source and the second x-ray detector are isocentric with the isocenter. Data received from the first x-ray detector is processed such that all projection radiographs of the object acquired from all scan angles are reconstructed to generate cross-sectional images of the object to guide simultaneously the radiation therapy treatment.

In another exemplary embodiment, a method for implementing 4-dimensional digital tomosynthesis using a system having an x-ray source and an x-ray detector includes steps as follows. A periodic motion of an object is divided into (n+1) time intervals, n being a positive integer, each of the (n+1) time intervals being associated with a time instance $t_i$, i=0, 1, 2, ..., n. The x-ray detector is used to acquire, for each scan angle, projection radiographs of the object at each time instance $t_i$ based on x-ray beams emitted by the x-ray source to the object. Digital tomosynthesis is used to reconstruct all projection radiographs acquired from all scan angles for each time instance $t_i$. (n+1) sets of cross sections of the object are obtained. The reconstructed cross sections are along one orientation only, e.g., either coronal cross sections or sagittal cross sections. Each of the (n+1) sets of cross sections is for a different time instance $t_i$.

It is to be understood that both the foregoing general description and the following detailed description are exemplary and explanatory only and are not necessarily restrictive of the invention as claimed. The accompanying drawings, which are incorporated in and constitute a part of the specification, illustrate an embodiment of the invention and together with the general description, serve to explain the principles of the invention.

BRIEF DESCRIPTION OF THE DRAWINGS

The numerous advantages of the present invention may be better understood by those skilled in the art by reference to the accompanying figures in which.

DETAILED DESCRIPTION OF SPECIFIC EMBODIMENTS

Reference will now be made in detail to the presently preferred embodiments of the invention, examples of which are illustrated in the accompanying drawings.

Four-dimensional computed tomography (4D CT) has been the center of attention for radiation therapy of the lung. Retrospective gating is the preferred method of 4D CT acquisition. This method exploits an external device that measures the breathing cycle and divides that into a number of intervals. Each projection of the CT acquisition is then associated with a time interval. Later (thereby the term retrospective) these projections are binned according to the time interval during the breathing cycle. This method assumes that breathing is periodic and the acquisition takes place over several breathing cycles. At the end, a number of volumes are reconstructed, where each volume represents the patient at a particular time instance during the breathing cycle. The present invention uses DTS to reconstruct cross sections. Since DTS is a much faster method than the CT approach for obtaining cross sections, it is advantageous to provide a new DTS method and system useful in 4D radiation therapy where the time component is integrated into the three-dimensional radiation therapy process to deliver dose in view of target motion.

The present invention extends DTS to acquire volume imaging over time. It describes (1) how DTS may be extended to reconstruct cross sections of time varying objects; and (2) how DTS can be used on a radiation therapy apparatus to generate cross-sectional images of a patient as the gantry is rotating, which are used to simultaneously guide the radiation therapy treatment (i.e., 4D radiation therapy). The fact that DTS acquisition is done with limited angles therefore lends itself to a practical solution for 4D acquisitions and radiation delivery.

The present invention extends DTS to the time domain to achieve a practical means of acquiring data to reconstruct 3D cross sections of objects over time. Moreover, the present invention applies 4D DTS to radiation therapy as a means of tracking the lesion and gating radiation. This is based on the observation/fact that cross sections reconstructed from DTS have the highest fidelity along the 2D planes that are most relevant to radiation treatment. Furthermore, the present invention applies 4D DTS to 4D radiation therapy as a means of generating cross-sectional images on the fly to guide simultaneously the radiation therapy treatment.

DTS Data Accquisition and Reconstruction

Figure 1:
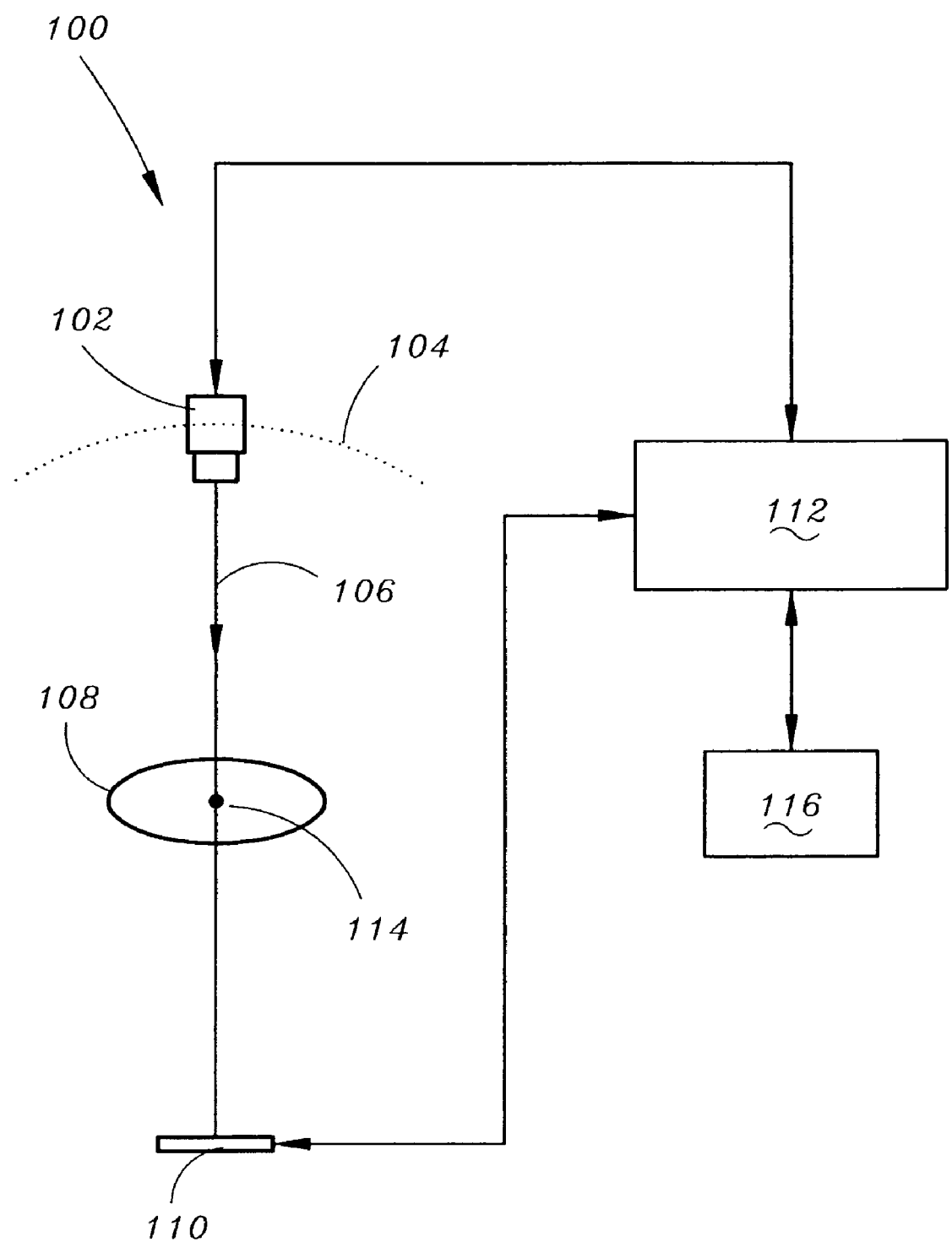
FIG. 1 is a block diagram illustrating a digital tomosynthesis system in accordance with an exemplary embodiment of the present invention.

FIG. 1 shows a DTS system 100. As shown in FIG. 1, the DTS system 100 includes an x-ray source (or tube) 102 that moves along an arc 104 and emits x-rays 106. X-rays 106 impinge upon an object (e.g., a patient) 108 and are detected by a x-ray detector 110. The object 108 contains typically 3-dimensional structures with different x-ray attenuation characteristics. The detector 110 is controlled by, and provides input to, a processor 112. The processor 112 executes processes, including controlling movement of the x-ray source 102 and readout of the detector 110, interpolating data from the detector 110 and reconstructing a 3-dimensional image of the object 108 from data (projection radiographs) detected by the detector 110, and other, auxiliary processing and control functions. Thus, for the object 108, the digital tomosynthesis system 100 acquires several projection radiographs in which the position of the x-ray source 102 changes relative to the object 108. Typically, this is accomplished by moving the x-ray source 102 and the detector 110 relative to the object 108 between acquisitions. Preferably, the x-ray source 102 and the detector 110 are locked together and rotate about a fixed central point 114 (i.e., isocentric motion). From the acquired projection radiograph images, the processor 112 reconstructs 3-dimensional information about the imaged object 108, and displays the resulting, reconstructed images. Typically, control and 3-dimensional reconstruction are performed within the processor 112, and the reconstructed image is displayed on a display screen 116. After reconstructing the 3-dimensional structure of the imaged object from data detected by the detector 110, the processor 112 provides that reconstruction data to the image display 116, which displays the reconstructed, 3-dimensional image to an operator.

Data acquisition for DTS may be achieved using numerous source and detector geometries and scan paths. An isocentric DTS system is preferred (see James T. Dobbins III and Devon J. Godfrey, *Digital x-ray Tomosynthesis: Current state of the art and clinical potential*, Physics in Medicine and Biology. 48 (2003) R65–R106). Although the isocentric scan path is preferred, the present invention is applicable to all type of Digital Tomosynthesis.

Figure 2:
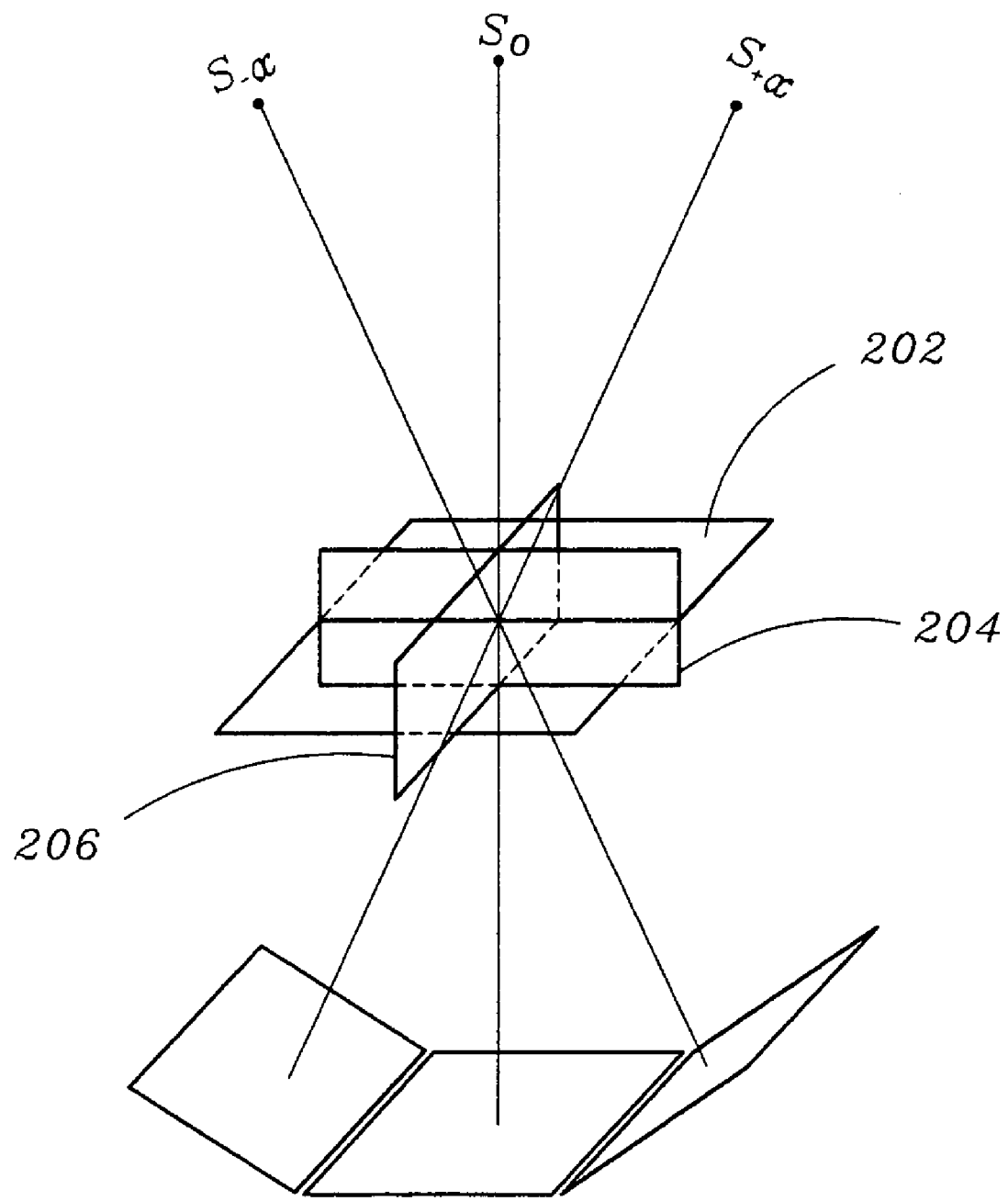
FIG. 2 is a schematic diagram illustrating a scan path and a coordinate system of isocentric digital tomosynthesis, where the X-ray source and the 2D detector are rotated around the object from $-\alpha$ to $+\alpha$ and a radiographic projection is acquired at every angular interval.

FIG. 2 illustrates the geometry and scan path of an isocentric DTS system. The X-ray source (either a kilovoltage or a megavoltage x-ray source) and the 2D detector are rotated around an object from $-\alpha$ to $+\alpha$ and a radiographic projection is acquired at every angular interval, e.g. once every degree. The projection images are then used to reconstruct cross sections of the 3D object. Considering the geometry, the coronal plane 202 is orthogonal to the principal axis of the radiation beam when the source is at angle 0. In this case, the coronal cross sections are reconstructed with higher image quality relative to the axial plan 204 and the sagittal plane 206.

Figure 3:
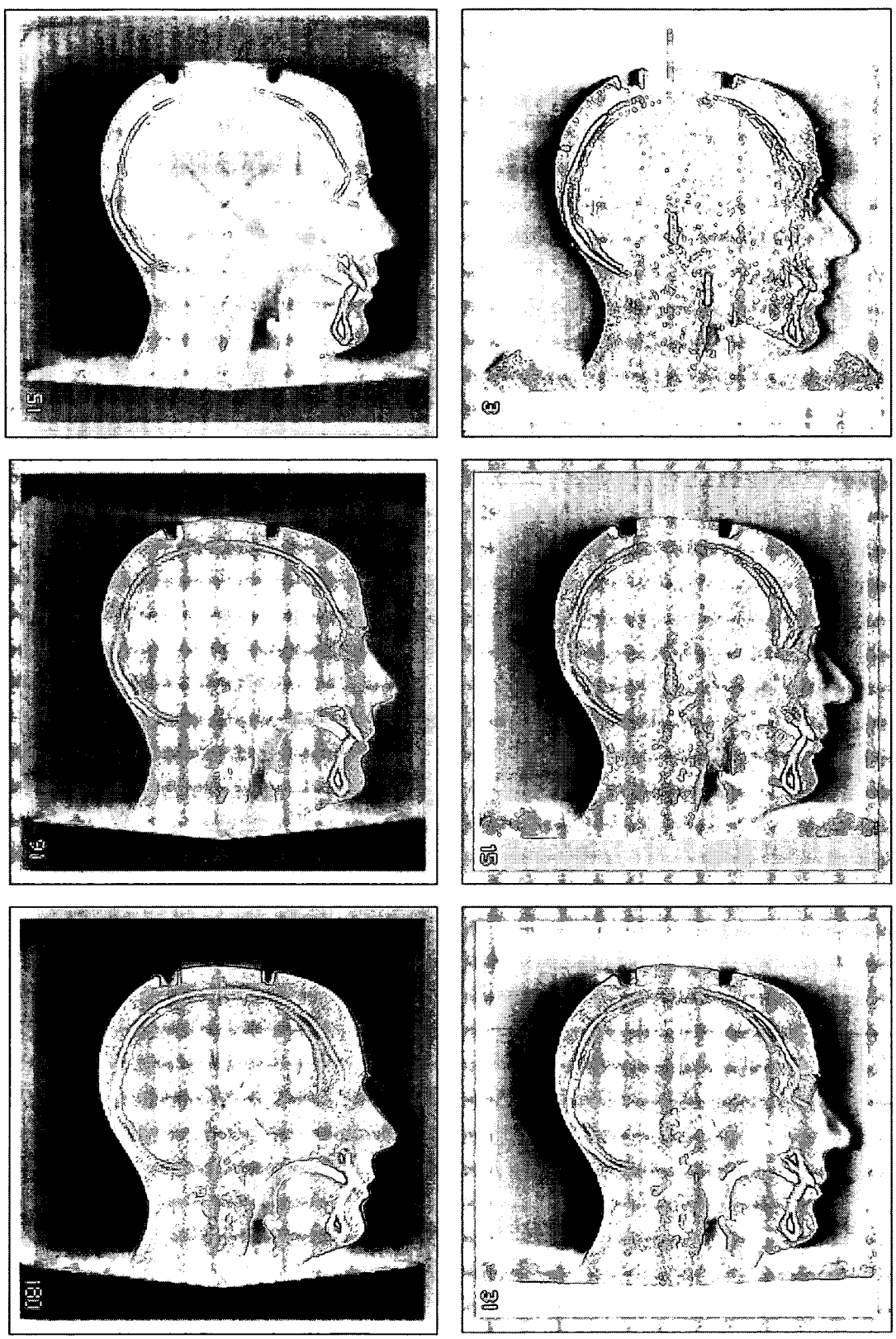
FIG. 3 shows DTS reconstructed images of an Alderson Rando head phantom using limited angle acquisitions in accordance with an exemplary embodiment of the present invention, where the number shown at the bottom-right corner on each image is the $\alpha$ value while the projections are taken at every two degrees.

When the scan angle of $-\alpha$ to $+\alpha$ increases to 180° plus the fan/cone angle, DTS converges to cone beam CT, where the reconstruction of the central axial plane becomes exact. FIG. 3 shows reconstructed coronal cross sections for different values of $\alpha$.

Figure 4A:
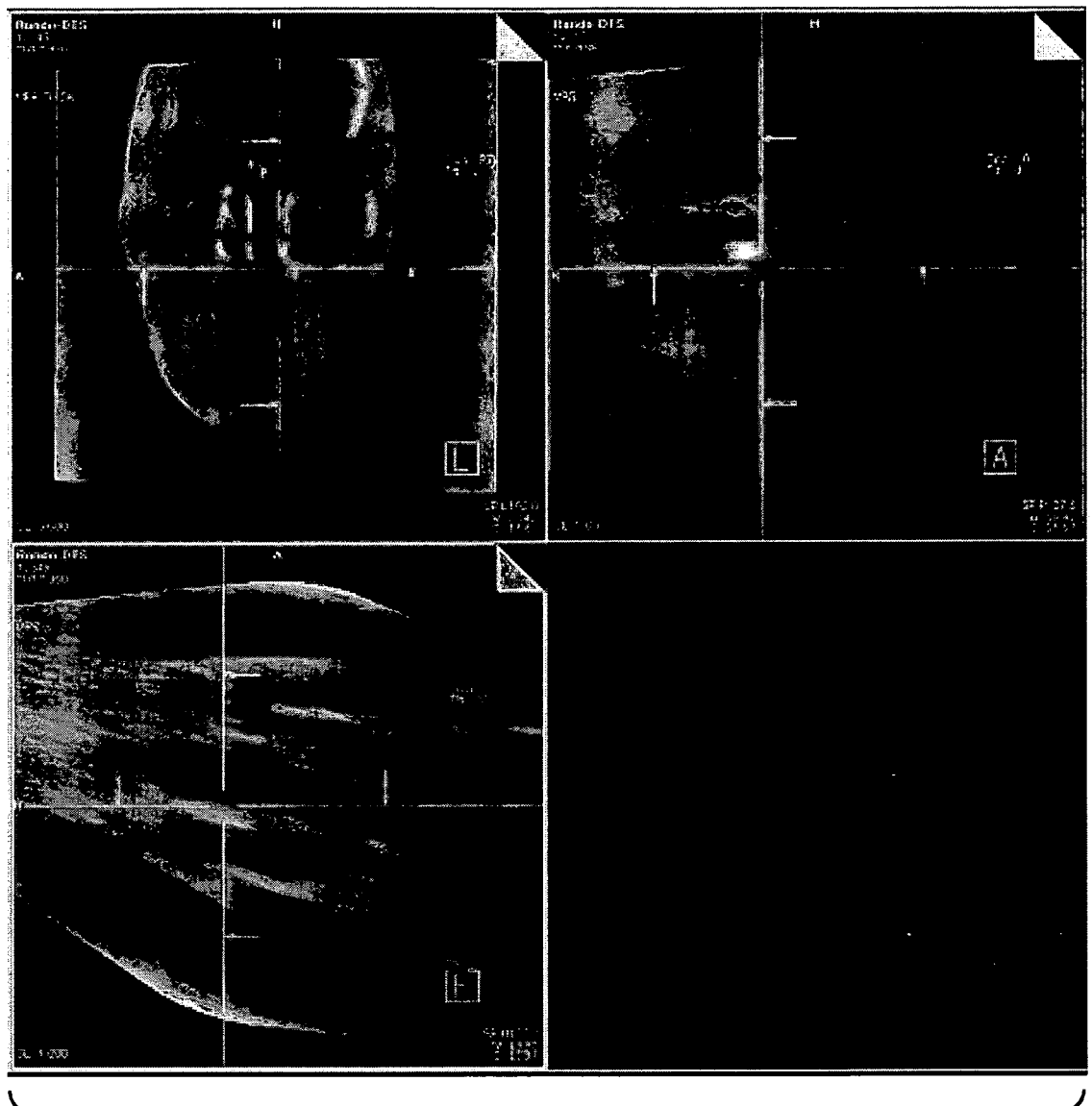
FIG. 4A shows three reconstructed cross sections after digital tomosynthesis of the Rando head phantom in accordance with an exemplary embodiment of the present invention.
Figure 4B:
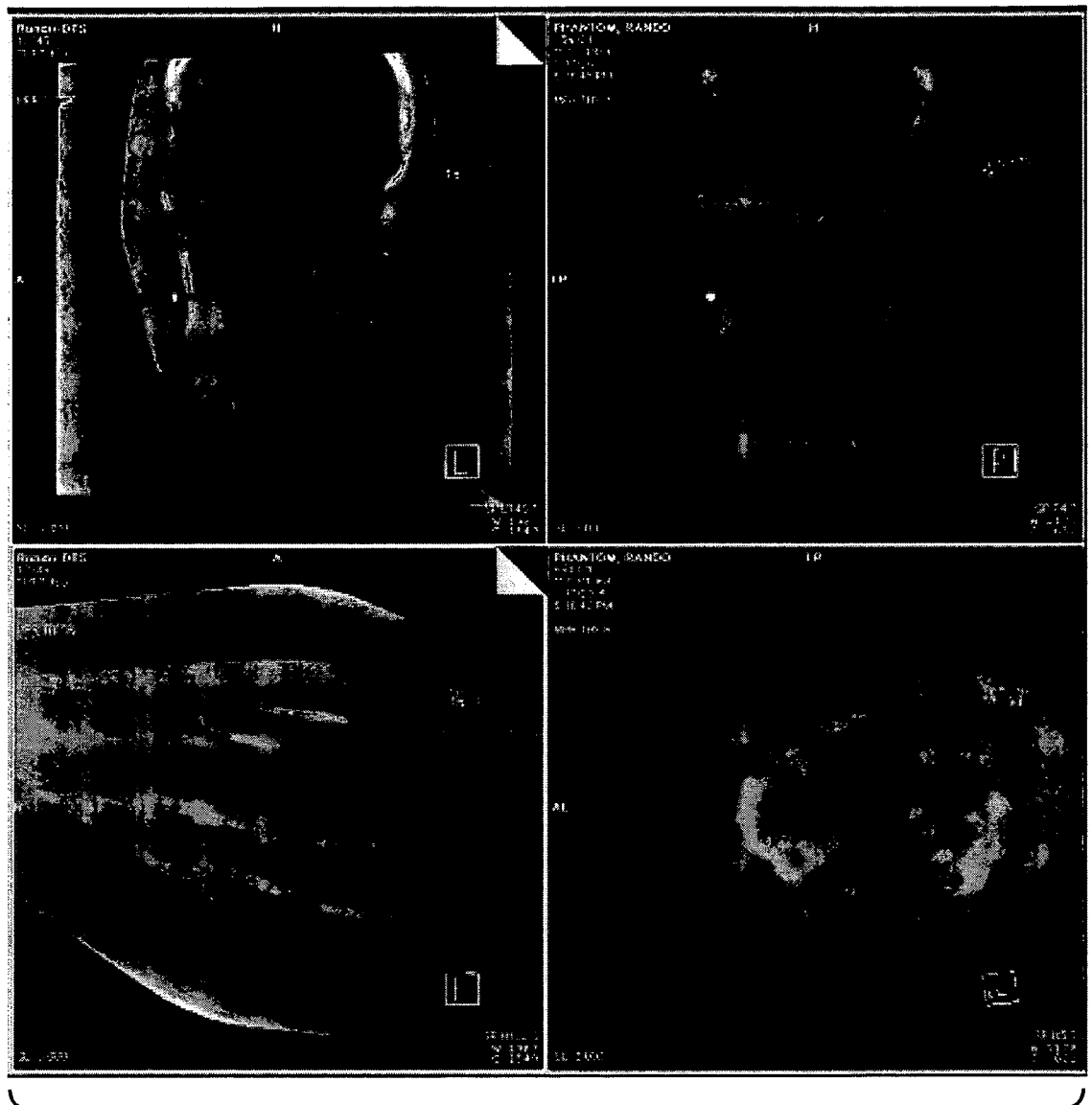
FIG. 4B shows coronal and transaxial cross sections of a Rando head phantom reconstructed based on digital tomosynthesis (left) as compare to that based on cone beam CT (right) in accordance with an exemplary embodiment of the present invention.

It is important to note that with small scan angles, the axial and sagittal cross sections may have poor image quality. However, the quality of the coronal images may be quite acceptable. One could imagine that DTS reconstructs thick coronal cross sections. The larger the scan angle, the finer/thinner the coronal cross sections may become. At the ultimate of 180° plus the fan/cone angle, the coronal cross sections may be infinitely thin. That would also result in the exact reconstruction of axial and sagittal cross sections. FIG. 4A illustrates DTS reconstruction of a Rando head phantom from 30° angle (i.e., $\alpha=30°$). As shown, the transaxial and sagittal cross sections are very poor, while the coronal cross sections (the upper left image) are good enough to show the internal anatomy. FIG. 4B illustrates a comparison between DTS with 30° acquisition angle and cone beam reconstruction with 200° acquisition angle (i.e. complete acquisition).

Figure 5:
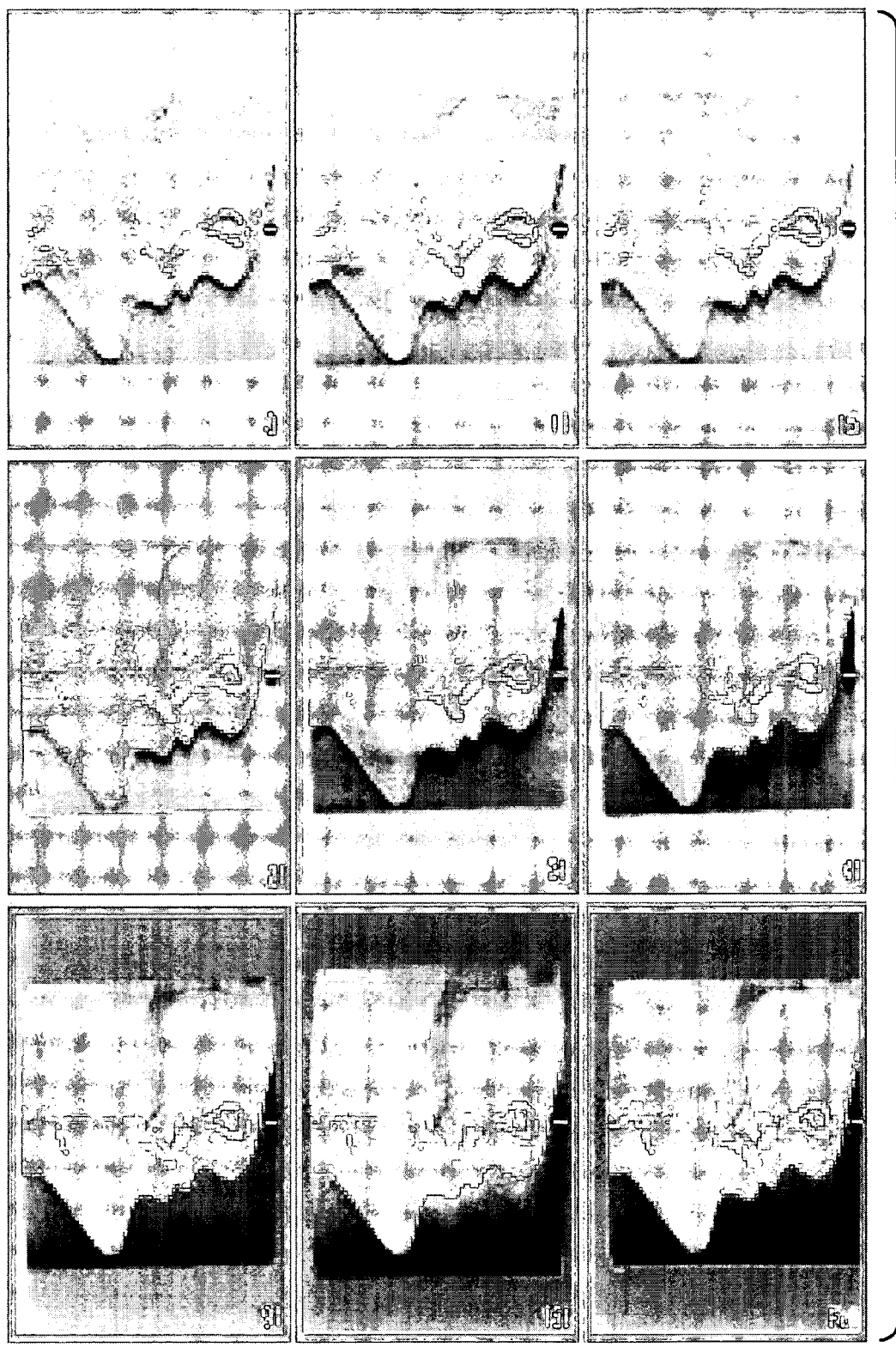
FIG. 5 shows same images as in FIG. 2, but using small field of view portals (local tomography)
Figure 6:
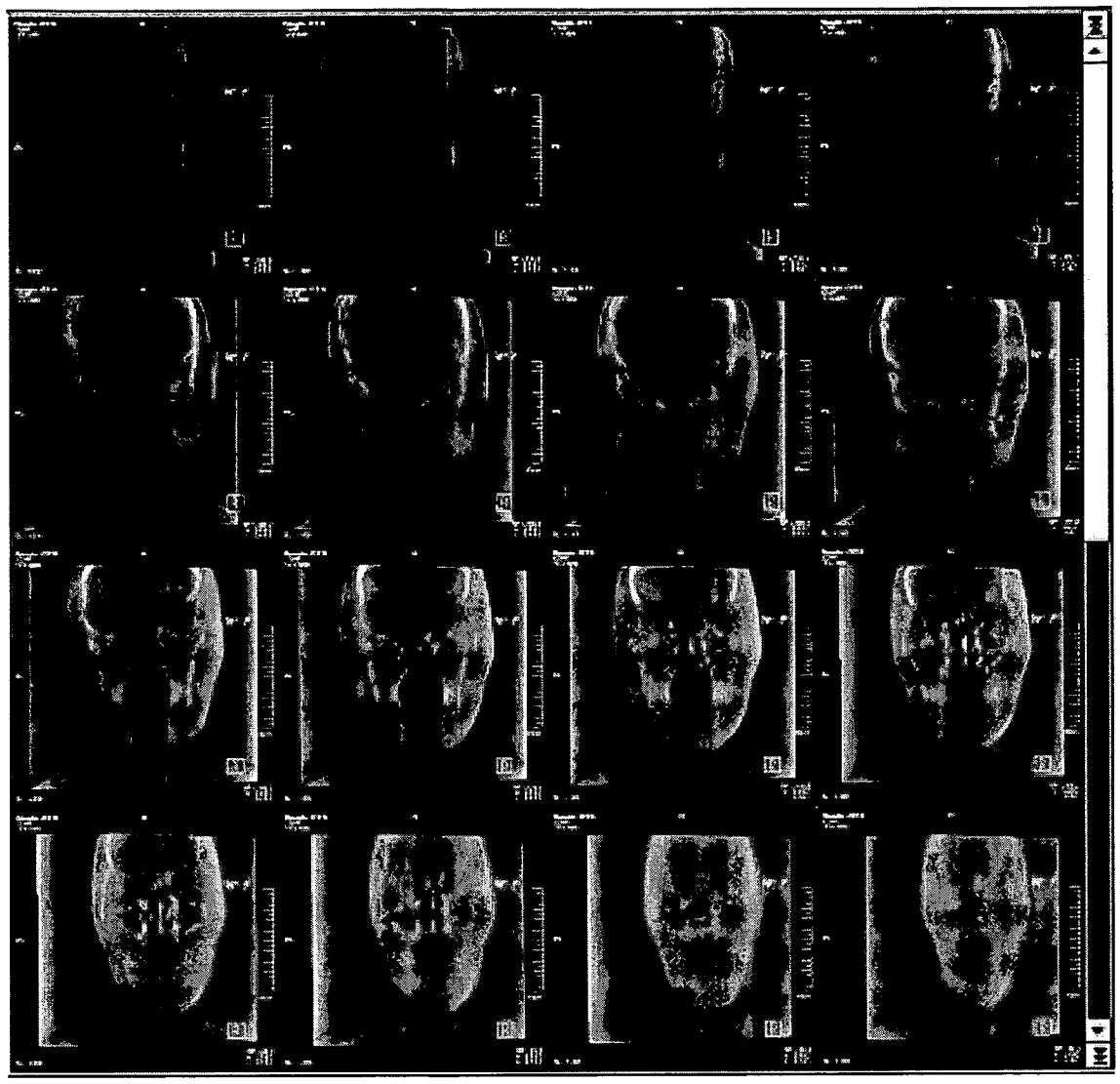
FIG. 6 shows different coronal cross sections of the Rando head phantom after DTS reconstruction from a 30° acquisition angle in accordance with an exemplary embodiment of the present invention.

It is noted that in the example in FIG. 3 x-ray field sizes large enough to image the entire Rando head phantom are used. Such large fields are not necessary. FIG. 5 shows the coronal cross sections reconstructed from images taken with smaller field sizes. FIG. 6 shows the different coronal cross sections of the Rando head phantom reconstructed from 30° acquisition angle.

When the treatment source (such as a megavoltage source on a linear accelerator) is at angle 0, the reconstruction of the coronal cross sections provides most of that is required for guiding the treatment beam (In general, the reconstruction of the cross sections that are orthogonal to the principal axis of the radiation beam contains most of that is required for guiding the treatment beam at any gantry angles). Since DTS only uses projections from limited angles to reconstruct the coronal images, it provides a faster way than the cone beam CT approach to locate the treatment target during radiation therapy (In order to minimize acquisition time, $\alpha$ needs to kept at a minimum, while the coronal cross sections are reconstructed with acceptable image quality). Thus, the present invention uses DTS as an alternative to the cone beam CT approach for treatment verification during radiation therapy. Furthermore, the present invention extends a DTS method of 3D image reconstruction to include the time domain.

Extension to Time Domain

This section describes how DTS may be extended to reconstruct cross sections of time varying objects, and how DTS can be used on a radiation therapy machine to generate cross-sectional images of a patient, which can be used to guide simultaneously the radiation therapy treatment (i.e., 4D radiation therapy). Although the applications given here are in the field of radiation therapy, the present invention is applicable to any other fields where rapid volumetric or tomographical imaging of an object is required.

I. Tracking and Gating for Objects with Periodic Motion

Similar to 4D CT, the present invention utilizes gating the image acquisition by an external device that monitors a physiological function, e.g. breathing. The breathing cycle is divided into (n+1) time intervals, n being a positive integer. Each time interval is associated with a time instance $t_i$, i=0, 1, 2, ..., n. At every angle, a series of images are acquired and associated with each time instance $t_i$. For each angle projection images for every time instance of the breathing cycle are acquired. Projections from all angles that are associated with each time instance $t_i$ are then reconstructed using DTS. This results in (n+1) sets of coronal cross sections. Each cross section may then be played in a cine mode to show the organ's motion throughout the entire breathing cycle.

Figure 7A:
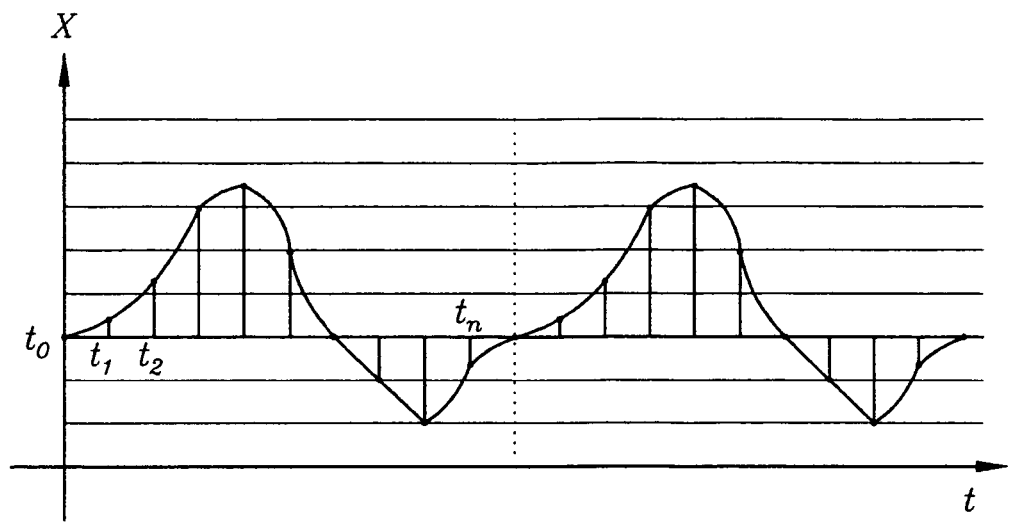
FIG. 7A shows a periodic physiological activity divided into a number of time intervals in accordance with an exemplary embodiment of the present invention.
Figure 7B:
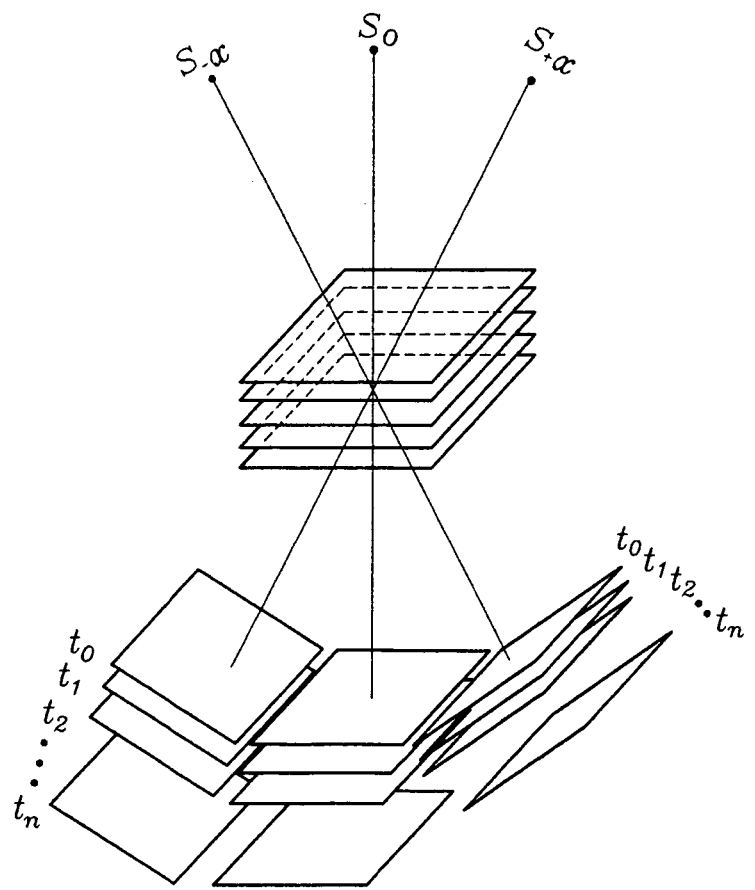
FIG. 7B is a depiction of how DTS acquisition is performed over time in accordance with an exemplary embodiment of the present invention.
Figure 7C:
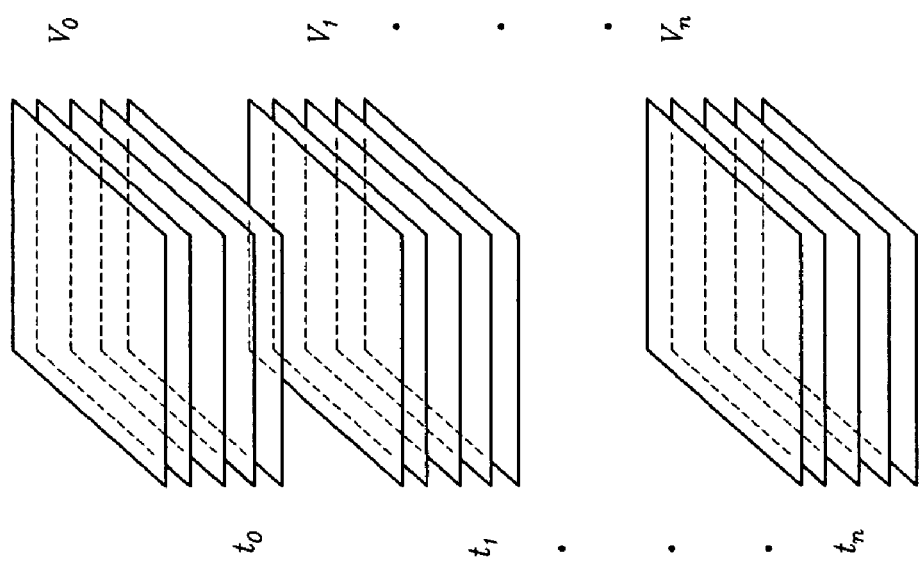
FIG. 7C shows series of cross section after DTS acquisition is performed over time, each representing the object at a time instance in accordance with an exemplary embodiment of the present invention.

FIGS. 7A, 7B and 7C illustrate the 4D DTS acquisition. FIG. 7A illustrates a periodic signal that is generated from an external device representing a physiological activity. This signal is broken into (n+1) time intervals. FIG. 7B illustrates how at each angle a series of projections are acquired over the entire cycle. At the end, the coronal cross sections of the body are reconstructed that represent the subject at each time instance of the cycle (see FIG. 7C).

II. Simultaneous Tomographical Imaging and Treatment

A. Therapy Machine

Figure 8:
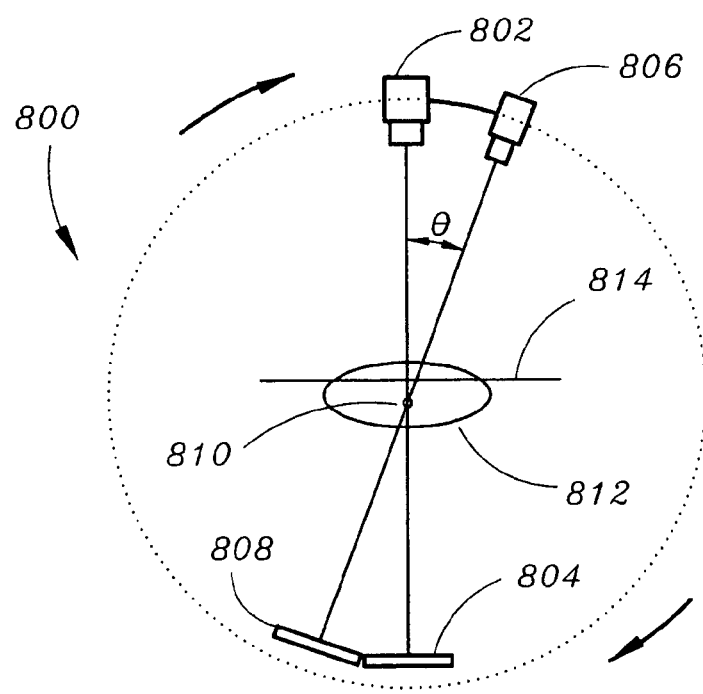
FIG. 8 shows a radiation treatment unit for simultaneous tomographical imaging and treatment in accordance with an exemplary embodiment of the present invention.

The present 4D digital tomosynthesis radiation therapy apparatus 800 for simultaneous tomographical imaging and treatment is shown in FIG. 8. The apparatus 800 includes a treatment system comprising a megavoltage (MV) x-ray source 802 (as the treatment source) and a MV x-ray detector 804; and (2) an imaging system comprising a kilovoltage (kV) x-ray source (or tube) 806 and a kV x-ray detector 808. All these components are mounted on the same gantry with the kV components having an angle of θ to the MV components. The angle θ can be either permanently fixed or adjustable, and can be anywhere from 0 degrees to 360 degrees. Typically θ is ~15–30 degrees. Both the treatment and imaging systems are isocentric with a single isocenter 810 and can be rotated simultaneously around an object 812 such as a patient, an animal, or the like. A plane of reconstruction 814 is orthogonal to the principal axis of the radiation beam emitted from the MV x-ray source 802 at angle 0. The kV x-ray tube and detector combination is used to obtain tomographical images of the treatment target (e.g., the lung of a patient or animal) for geometrical verification. The MV x-ray source and detector combination is for dose delivery and dose reconstruction. Thus, the imaging system provides the Just-In-Time tomographical imaging information (i.e., the right amount of tomographical imaging information at the right time) of the treatment target (object). This information is then used to the guide the treatment beam immediately.

B. Rapid Tomographical Imaging

Figure 9:
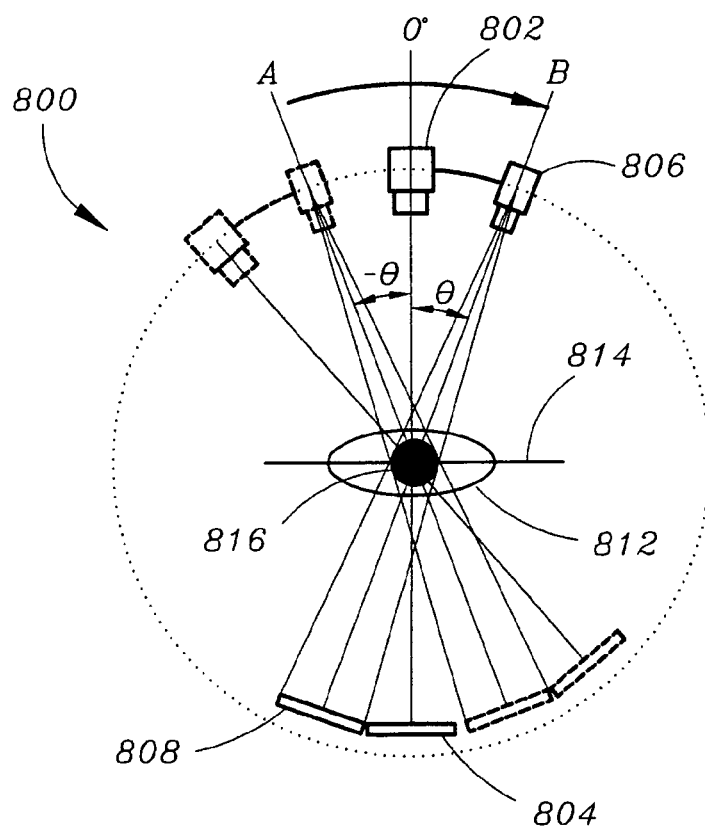
FIG. 9 shows rapid tomographical imaging by rotating the kV tube (and the kV detector) from A to B to perform DTS, where the plane of DTS reconstruction is orthogonal to the principal axis of the MV beam in accordance with an exemplary embodiment of the present invention.

FIG. 9 illustrates how to use the treatment apparatus 800 to perform DTS by rotating the kV imaging system around the living thing 812 from position A to B. If the scan angle α is set to be equal θ, then the plane of DTS reconstruction 814 is orthogonal to the principal axis of the MV beam at the end of the rotation (i.e., when the kV x-ray tube 806 is at location B). Thus, at the end of the rotation, the DTS reconstructed images can be used to guide the treatment beam immediately to treat a target 816 (e.g., the lung of a patient or animal).

Figure 10:
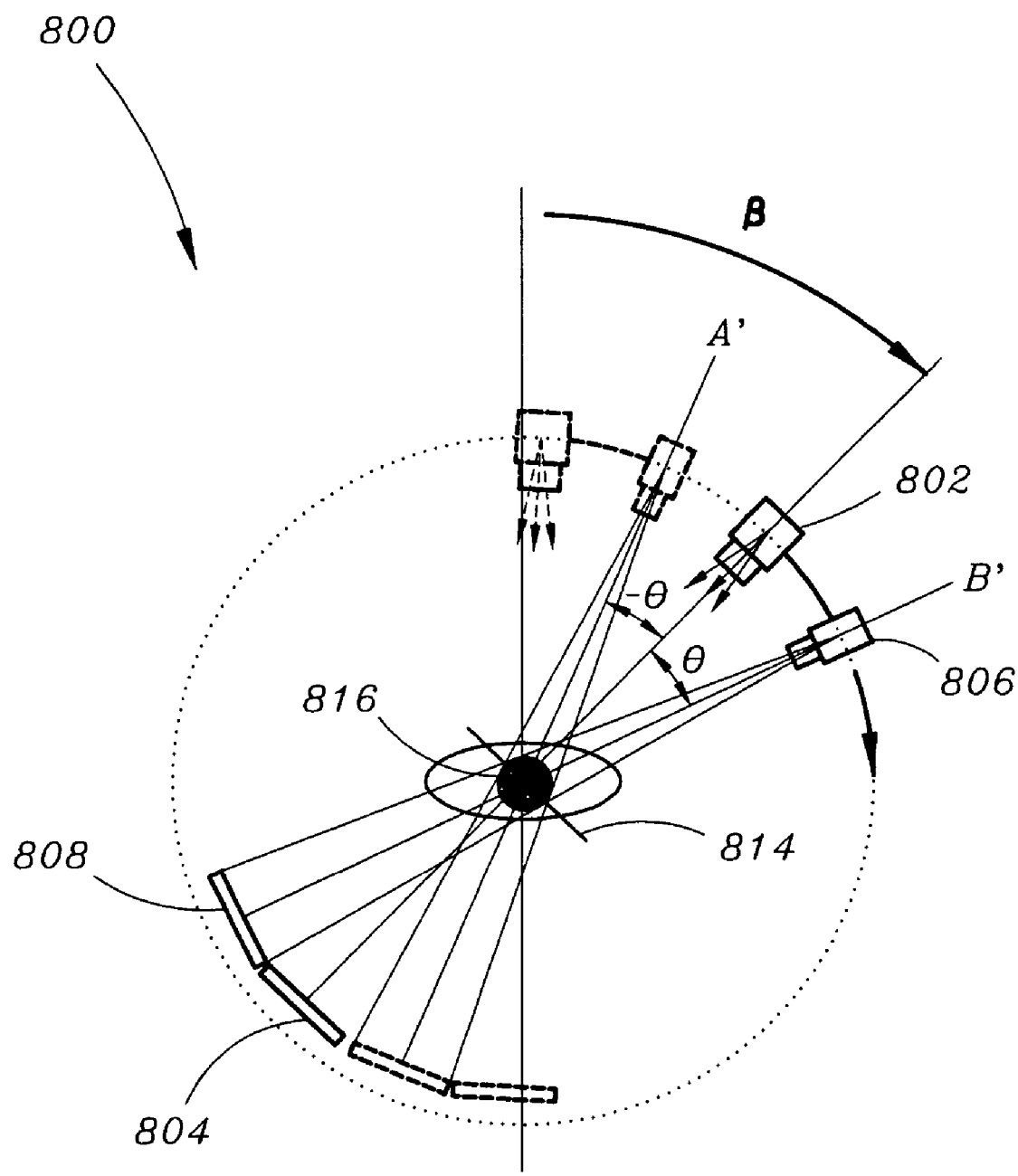
FIG. 10 shows tomographical imaging in real time, where the plane of DTS reconstruction is always orthogonal to the principal axis of the MV beam in accordance with an exemplary embodiment of the present invention.

FIG. 10 illustrates how to use the treatment apparatus 800 to obtain tomographical images of the target 816 on the fly to guide the radiation therapy treatment. When the gantry continues to rotate from a location, new kV x-ray projection images are taken for each gantry increment Δ. New DTS cross-sectional images are reconstructed on the fly by (1) adding only new projection images taken during the increment; and (2) removing the same number of projection images taken earlier so that only projection images taken within gantry angle [β−θ, β+θ] are used in the reconstruction (see FIG. 10). This keeps the tomographical imaging information updated. The plane of DTS reconstruction is always orthogonal to the principal axis of the MV beam at any given gantry angle. Thus, the most-recently-updated tomographical imaging information can be used to guide the radiation therapy treatment in real time, and tomographical imaging and treatment can be performed simultaneously while the gantry is being rotated.

C. Modes of Operation

Figure 11:
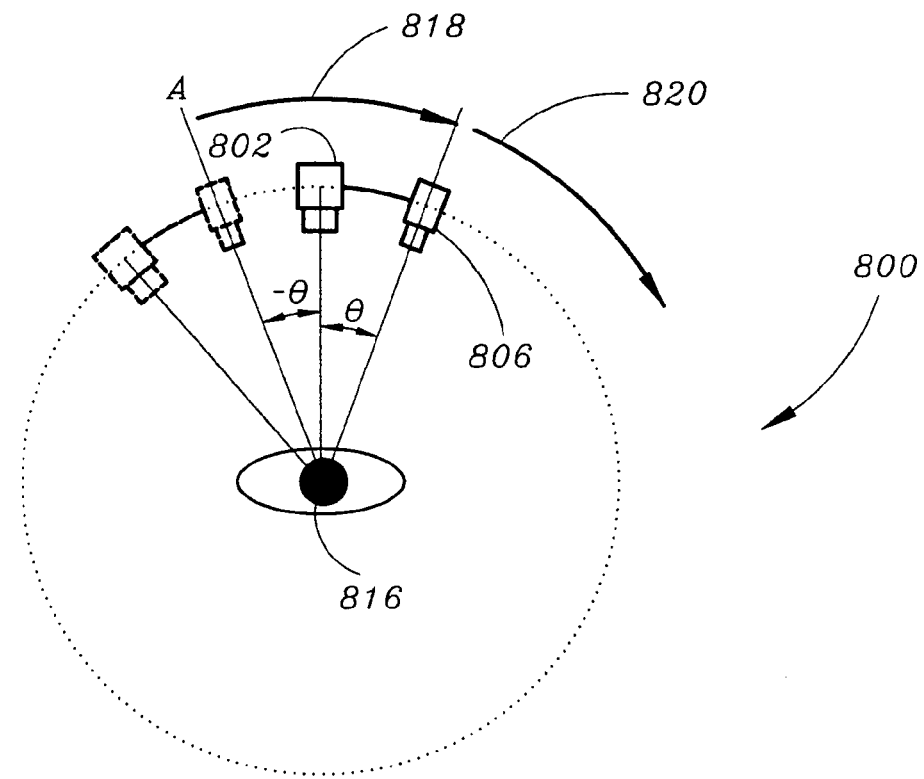
FIG. 11 shows a continuous mode of operation, where imaging and treatment are performed simultaneously in accordance with an exemplary embodiment of the present invention.
Figure 12:
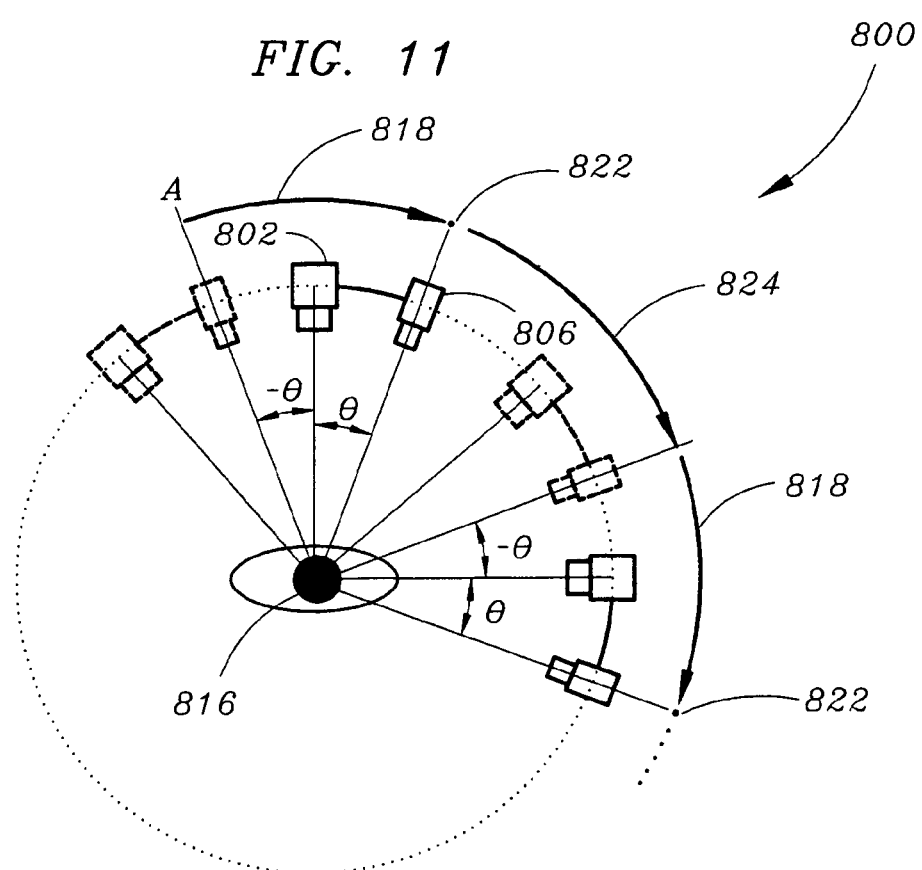
FIG. 12 shows a step-and-shoot mode of operation, where imaging is performed before treatment is performed in accordance with an exemplary embodiment of the present invention.

There are, at least, two possible modes of operations: (1) Continuous mode where imaging and treatment are performed simultaneously once the 1st DTS reconstruction is completed, as illustrated in FIG. 11, where an arc 818 is for imaging only, and an arc 820 is for simultaneous imaging and treatment; (2) The step-and-shoot mode where imaging is performed first, followed by the treatment, as shown in FIG. 12, where the arc 818 is for imaging only, location 822 is for treatment only, and an arc 824 is for rotation only. In both modes, the updated tomographical imaging information is used to guide the radiation therapy treatment.

D. Possible Variations

The therapy unit 800 shown in FIG. 8 is a preferred embodiment for performing simultaneous tomographical imaging and treatment. However, there are possible variations. These include but are not limited to the following situations. First, the x-ray tube 806 can be on the other side of the gantry, i.e., θ→180°±θ or 360°±θ. Additionally, the angle θ can be 0 degrees or 180 degrees. In this case, the present invention still applies and rapid tomographical imaging can still be performed. However, the plane of DTS reconstruction is no longer orthogonal to the principal axis of the MV beam. The gantry has to be reversed by α degrees in order to treat the target based on DTS reconstructed images. Thus, the mode of operation may be more likely a "step-forward-then-backward-and-shoot" mode. There is no continuous mode (where tomographical imaging and treatment are performed simultaneously). Moreover, there can be only one x-ray source (and one x-ray detector). In this case, the x-ray source is used for both DTS and treatment. Once again, the mode of operation may be a "step-forward-then-backward-and-shoot" mode. Furthermore, there can be more than one kV imaging systems, e.g., one more x-ray tube can be added at the left side of the MV source in FIG. 8. In this case, the continuous mode works for both clockwise and anti-clockwise rotations.

It is understood that the specific order or hierarchy of steps in the foregoing disclosed methods are examples of exemplary approaches. Based upon design preferences, it is understood that the specific order or hierarchy of steps in the method can be rearranged while remaining within the scope of the present invention. The accompanying method claims present elements of the various steps in a sample order, and are not necessarily meant to be limited to the specific order or hierarchy presented.

It is believed that the present invention and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely an explanatory embodiment thereof, it is the intention of the following claims to encompass and include such changes.

What is claimed is:

1. A 4-dimensional digital tomosynthesis system, comprising;
    an x-ray source for emitting x-ray beams to an object, the object having a periodic motion being divided into (n+1) time intervals, n being a positive integer, each of the (n+1) time intervals being associated with a time instance $t_i$, i=0, 1, 2, . . . , n;
    an x-ray detector, coupled to the x-ray source, for acquiring projection radiographs of the object at each time instance $t_i$, for each scan angle based on the x-ray beams; and
    a processor communicatively coupled to the x-ray source and the x-ray detector, the processor configured to control the x-ray source and process data received from the x-ray detector such that all projection radiographs acquired from all scan angles for each time instance $t_i$ through digital tomosynthesis are reconstructed and (n+1) sets of cross sections of the object are obtained, each of the (n+1) sets of cross sections being for a different time instance $t_i$.

2. The 4-dimensional digital tomosynthesis system as claimed in claim 1, wherein the processor plays each of the (n+1) sets of cross sections in a cine mode to show the periodic motion of the object.

3. The 4-dimensional digital tomosynthesis system as claimed in claim 1, wherein the object is at least one lung of a living thing.

4. The 4-dimensional digital tomosynthesis system as claimed in claim 1, wherein the x-ray source and the x-ray detector are positioned for isocentric motion.

5. The 4-dimensional digital tomosynthesis system as claimed in claim 1, wherein the x-ray source is a megavoltage x-ray source or a kilovoltage x-ray source.

6. The 4-dimensional digital tomosynthesis system as claimed in claim 1, wherein the x-ray source provides treatment of the object by way of dose delivery and dose reconstruction.

7. A radiation therapy apparatus, comprising:
a 4-dimensional digital tomosynthesis imaging system including a first x-ray source and a first x-ray detector for obtaining tomographical images of a treatment target for geometrical verification, the first x-ray source and the first x-ray detector being isocentric with an isocenter, the treatment target being an object with a motion, the first x-ray source for emitting x-ray beams to the object, the first x-ray detector for acquiring projection radiographs of the object for each scan angle based on the x-ray beams;
a treatment system, including a second x-ray source and a second x-ray detector for dose delivery, the second x-ray source and the second x-ray detector being isocentric with the isocenter; and
a processor configured to process data received from the first x-ray detector,
wherein data received from the first x-ray detector is processed such that all projection radiographs of the object acquired from all scan angles are reconstructed to generate cross-sectional images of the object on the fly to guide radiation therapy treatment of the object using the treatment system, wherein said radiation therapy apparatus is configured to operate in a step-and-shoot mode.

8. The radiation therapy apparatus as claimed in claim 7, wherein the motion is a periodic motion divided into (n+1) time intervals, n being a positive integer, each of the (n+1) time intervals being associated with a time instance $t_i$, i=0, 1, 2, . . . , n, wherein (n+1) sets of cross sections of the object are obtained, each of the (n+1) sets of cross sections being for a different time instance $t_i$, and wherein each of the (n+1) sets of cross sections is played in a cine mode to show the periodic motion of the object, the (n+1) sets of cross sections being coronal cross sections or sagittal cross sections.

9. The radiation therapy apparatus as claimed in claim 7, wherein the object is at least one lung of a living thing.

10. The radiation therapy apparatus as claimed in claim 7, wherein the first x-ray source is a kilovoltage x-ray source and the second x-ray source is a megavoltage x-ray source.

11. The radiation therapy apparatus as claimed in claim 7, wherein the first x-ray source is positioned with respect to the isocenter so that an angle θ is formed between a line connecting the first x-ray source and the isocenter and a line connecting the second x-ray source and the isocenter, $0° \leq \theta \leq 360°$.

12. The radiation therapy apparatus as claimed in claim 11, wherein θ is permanently fixed or adjustable.

13. The radiation therapy apparatus as claimed in claim 11, wherein $15° \leq \theta \leq 30°$.

14. A method for implementing 4-dimensional digital tomosynthesis using a system having an x-ray source and an x-ray detector, comprising:
dividing a periodic motion of an object into (n+1) time intervals, n being a positive integer, each of the (n+1) time intervals being associated with a time instance $t_i$, i=0, 1, 2, . . . , n;
using the x-ray detector to acquire, for each scan angle, projection radiographs of the object at each time instance $t_i$ based on x-ray beams emitted by the x-ray source to the object;
using digital tomosynthesis to reconstruct all projection radiographs acquired from all scan angles for each time instance $t_i$; and
obtaining (n+1) sets of cross sections of the object, each of the (n+1) sets of cross sections being for a different time instance $t_i$.

15. The method as claimed in claim 14, further comprising:
playing each of the (n+1) sets of cross sections in a cine mode to show the periodic motion of the object.

16. The method as claimed in claim 14, wherein the object is at least one lung of a living thing.

17. The method as claimed in claim 14, wherein the x-ray source and the x-ray detector are positioned for isocentric motion.

18. The method as claimed in claim 14, wherein the x-ray source is a megavoltage x-ray source or a kilovoltage x-ray source.

19. The method as claimed in claim 14, wherein the x-ray source provides treatment of the object by way of dose delivery and dose reconstruction.

* * * * *